United States Patent [19]
Lange, III et al.

[11] 4,111,751
[45] Sep. 5, 1978

[54] METHOD OF PURIFYING ALCOHOL DEHYDROGENASE

[75] Inventors: Louis G. Lange, III; Bert L. Vallee, both of Brookline, Mass.

[73] Assignee: President and Fellows of Harvard College, Cambridge, Mass.

[21] Appl. No.: 847,706

[22] Filed: Nov. 2, 1977

Related U.S. Application Data

[63] Continuation-in-part of Ser. No. 640,629, Dec. 15, 1975, abandoned.

[51] Int. Cl.² ............................................. C07G 7/026
[52] U.S. Cl. ..................................... 195/66 R; 526/50; 536/112
[58] Field of Search ................................... 195/66 R

[56] References Cited

U.S. PATENT DOCUMENTS

| | | | |
|---|---|---|---|
| 3,912,595 | 10/1975 | Philipp et al. | 195/66 R |
| 3,920,631 | 11/1975 | Molteni et al. | 536/112 |
| 3,926,730 | 12/1975 | Huper et al. | 195/66 R |
| 3,951,744 | 4/1976 | Roder et al. | 195/66 R |
| 3,970,603 | 7/1976 | Gray | 526/50 |
| 4,030,997 | 6/1977 | Fujii et al. | 195/66 R |

OTHER PUBLICATIONS

Li et al., Biochem. Biophys. Res. Comm. 63, 202–208 (1975).

*Primary Examiner*—Lionel M. Shapiro

[57] ABSTRACT

An affinity resin containing pyrazole immobilized on a solid insoluble support by a coupling arm bonded at the 4-position having a length of at least 12 Angstrom units is used to purify and fractionate crude alcohol dehydrogenase extract into a pyrazole-binding fraction and a pyrazole-insensitive fraction containing the anodic band by bringing the resin into contact with an aqueous solution of a binary complex of alcohol dehydrogenase and NAD to bind the binary complex, then eluting the complex. The bound fraction can be further fractionated into isoenzymes during elution by adjusting the alcohol gradient of the eluant, and the anodic band can be separated from the remainder of the solution, which does not bind to pyrazole, by salting out and chromatography on agarose-AMP resin.

11 Claims, No Drawings

METHOD OF PURIFYING ALCOHOL DEHYDROGENASE

This application is a continuation-in-part of application Ser. No. 640,629 filed Dec. 15, 1975, now abandoned.

This invention relates to a process for purifying and fractionating enzymes by affinity chromatography and pertains more specifically to the purification and fractionation of alcohol dehydrogenases, particularly liver alcohol dehydrogenases, and to an affinity resin for use in the process.

Enzymes such as alcohol dehydrogenases are useful in oxidizing various alcohols and glycols to aldehydes; indeed alcohol dehydrogenase from human liver has potential value for treating alcoholism because of its ability to oxidize ethanol. However, purification of these enzymes has been a complicated and difficult procedure. It has now been found that crude extracts of alcohol dehydrogenases can be purified and separated to provide products of high purity in high yield by an affinity chromatographic process in which a binary complex of the crude alcohol dehydrogenase with the coenzyme NAD is formed, then brought into contact with an affinity resin comprising an inhibitor such as pyrazole to which a portion of its binds, the pyrazole being immobilized on a solid insoluble support, after which the bound portion of the binary complex in highly purified form is eluted. Elution is preferably carried out with pyrazole solution or with a lower alkanol having at least two carbon atoms, e.g., ethanol, 1-propanol, 1-butanol, 1-pentanol, and the like. Further purification and separation of isoenzymes from the bound portion can be achieved by alcohol gradient elution. The alcohol dehydrogenase of the bound portion can be separated from the NAD after elution, if desired, by conventional dialysis procedures. Because the immobilized pyrazole is much more highly specific in binding the binary complex than it is in binding alcohol dehydrogenase alone, the process of the present invention provides alcohol dehydrogenase of much higher purity than can be obtained in the absence of NAD, or than can be obtained by using immobilized NAD derivatives. The anodic band of liver alcohol dehydrogenase, as identified by Li et al., Biochem. Biophys. Res. Comm. 63, 202 (1975), which does not bind to the affinity resin, can be separated from the remaining proteins of the pyrazole-insensitive material and from the NAD with which it has been complexed by salting out, for example by ammonium sulfate precipitation, and by affinity chromatography over agarose-AMP resin. This anodic band of liver alcohol dehydrogenase, which is herein called II-ADH, is strikingly different in properties from all other forms of liver alcohol dehydrogenase; not only is it remarkably insensitive to inhibition by pyrazole compounds ($K_I = 500$ μM), in contrast to the high affinity of all other forms of liver alcohol dehydrogenase for pyrazole and its 4-substituted compounds ($K_I$ less than 1 μM), but it exhibits a $K_m$ for ethanol of 15–30 mM at pH 7.5, as much as 100 times that of the other forms of liver alcohol dehydrogenase ($K_m = 1$ mM or less), suggesting that it may serve a unique role in the elimination of ethanol, and it displays lower electrophoretic mobility than other forms of liver alcohol dehydrogenase. The marked differences between these forms of liver alcohol dehydrogenase can be further characterized in terms of their enzyme activity in the presence of varying ethanol concentrations. At 100 mM ethanol, 0.2 mM 4-methylpyrazole inhibits the activity of purified II-ADH by less than 10%, while the remainder of the purified enzyme forms are inhibited more than 90%. In the absence of 4-methylpyrazole, enzyme activity in the crude liver extract increases progressively when measured over a range of ethanol concentration from 0.3 to 100 mM. However, in the presence of 0.2 mM 4-methylpyrazole, activity is observed only when ethanol concentration exceeds 3 mM and increases thereafter in parallel with that observed in the absence of 4-methylpyrazole. Thus, II-ADH begins to contribute significantly to total activity only at concentrations of ethanol above 5 mM, in accord with the known high $K_m$ for ethanol of this enzyme form. At ethanol concentrations approaching saturation for II-ADH, 100 mM, it accounts for 40% of the total activity in the crude liver extract.

The contribution of the pyrazole-sensitive forms to total activity was calculated from the difference in activity measured in the absence and presence of 4-methylpyrazole. Importantly, this activity becomes constant at about 5 mM ethanol, in agreement with the low $K_m$ for ethanol reported previously for these molecular forms.

The process comprises mixing the crude aqueous alcohol dehydrogenase extract with an aqueous solution containing NAD at a concentration of at least $10^{-4.5}$ molar and at a pH up to 8.0 to form a binary complex of the dehydrogenase with the NAD, bringing the mixture into contact with an affinity resin comprising pyrazole immobilized on an insoluble solid support, the pyrazole being covalently bonded at the 4-position to the support by a connecting arm or spacer (also called group or coupling arm) having a length of at least 12 Angstrom units, to bind a portion of the dehydrogenase and NAD to the support, and eluting the bound dehydrogenase and NAD from the support.

The crude aqueous extract containing alcohol dehydrogenase can be obtained from a variety of sources; in particular from livers of mammals such as horses, rats and rabbits as well as from human liver. Crude extracts obtained from other sources can also be used. The crude extract can be prepared, for example, by grinding up liver at 4° C. with twice its weight of water, removing gross impurities by straining, then filtering through a bed of diethylaminoethyl cellulose in particulate form (using 1 to 2.5 ml. of DEAE cellulose per gram of starting tissue), equilibrated at pH 7.9 with a buffer such as 0.01 molar tris-(hydroxymethyl) aminomethane. Under such conditions of pH and low ionic strength, the diethylaminoethyl cellulose binds and removes from the extract a large proportion of the total protein present but does not bind the alcohol dehydrogenases, which pass through into the filtrate along with residual foreign proteins.

The binary complex, in which two molecules of NAD are complexed with one molecule of alcohol dehydrogenase, can be prepared simply by mixing NAD with the crude extract of alcohol dehydrogenase. In order to ensure that substantially all of the alcohol dehydrogenase is present in solution in the form of the binary complex, it is desirable to employ an excess of the amount of NAD over that theoretically required. However, since the crude extract in practice always contains alcohol dehydrogenase in very low concentration, it is the dissociation constant of the complex (approximately $10-6$) which is controlling, and it is found that introduction of NAD in an amount sufficient to provide a concentration of $10^{-4.5}$ molar is sufficient to ensure that substantially all of the alcohol dehydrogenase is in the form of the binary complex. Although larger amounts of NAD can be used, there is no advantage in using a concentration above about $10^{-3}$ molar since optimum results are achieved at that concentration with no further improvement even when the concentration of the NAD is $10^{-2}$ molar or even higher, the results being approximately the same at these higher concentrations. The aqueous medium containing the binary complex may be acidified if desired. Satisfactory results are obtained at pH 8.0, but may be improved by decreasing the pH to approximately 7.5 in order to achieve optimum results; however, no further improvement is achieved by further lowering of the pH, the results remaining about the same even at a pH below 6.

The new affinity resin with which the aqueous medium containing the binary complex is brought into contact can be made by conventional techniques by first activating a solid insoluble support member which is a carbohydrate, particularly a polysaccharide such as carboxymethyl cellulose, agarose, agar, dextran, or the like, or which is a polyacrylamide, glass beads or the like, preferably in granular or particulate form suitable for packing into a column, by reacting the support material with cyanogen bromide or other suitable activator, then coupling pyrazole at the 4-position to the activated support by a group or coupling arm having a length of at least 12 Angstrom units. A group having the minimum effective length is provided, for example, when a compound such as 4-[3-(N-3-aminopropionyl)-aminopropyl]-pyrazole is coupled to an activated support. In this case, the coupling arm contains a chain of six carbon atoms and two nitrogen atoms to provide the necessary minimum length. Improved results can be achieved by using as a coupling arm a longer group, such as one containing a chain of nine carbon atoms and two nitrogen atoms having a length of approximately 16 Angstrom units found in the group 4-[3-(N-6-aminocaproyl)-aminopropyl]. Although longer coupling arms can be used, such as groups having a length of 27 Angstrom units or even more, an example of which is 4-[3-(6-[p-aminobenzoyl]-N-6-aminocaproyl)-aminopropyl], no further improvement in yield or purity is achieved when such longer coupling arms are employed, the results remaining about the same. The support which is preferred is a water-insoluble polysaccharide, particularly dextran; an affinity resin in which a water-insoluble polyacrylamide is the support is also preferred but is less desirable because it tends to lose its effectiveness after one to two weeks.

The coupling arm or connecting arm by which the pyrazole is covalently linked to the support is a group containing a chain of atoms which may include carbon, nitrogen and oxygen and which is at least 12 Angstrom units in length. One end of the group is covalently bonded to pyrazole at the 4-position, the other end carries a terminal amino or group which bonds covalently with the activated support. Coupling arms such as 4-(3-aminopropyl) and 4-[3-(N-2-aminoacetyl)-aminopropyl] which have lengths of approximately 6 and 10 Angstrom units, respectively, produce affinity resins having poor binding capacity for the binary complex, whereas the affinity resins made with coupling arms 12 Angstrom units or more in length having binding capacities for the binary complex many times as high. There is no critical upper limit on the length of the coupling or connecting arm beyond that of convenience and economy of manufacture since increase in length has no substantial adverse effect upon the use of the affinity resin for the purpose of the present invention.

In the case of dextran activated with 300 mg. of cyanogen bromide per ml. of dextran, the binding capacity of the affinity resin increased with increasing quantities of pyrazole compound added to the activated dextran to a maximum of 4.85 mg./ml. at approximately 29 millimoles pyrazole compound per liter of reaction mixture, 50% dextran by volume. This affinity resin contained 6.45 micromoles of pyrazole compound per ml. of dextran, the binding capacity being 0.91% of the theoretical. In the case of dextran activated with 180 mg. of cyanogen bromide per ml. of dextran, binding capacity of the affinity resin continued to increase as the amount of pyrazole compound increased above 50 millimoles per liter of reaction mixture. Dextran activated with even less cyanogen bromide, even as little as 100 mg. per ml. or less, can be used if larger concentrations of pyrazole compound are employed.

For best results, it is desired that the total ionic strength of the aqueous medium containing the binary complex brought into contact with the affinity resin be maintained at a level from 0.05 to 0.30. An ionic strength within the desired range can be provided, for example, by adding sufficient phosphate buffer to the aqueous medium containing the binary complex so as to provide a concentration of 50 millimolar phosphate.

In carrying out the process of the invention, the granular support on which pyrazole has been immobilized to form the affinity resin is preferably employed in the form of a column through which the aqueous medium containing the binary complex is caused to flow. A portion of the binary complex is selectively retained by the column and can subsequently be eluted from the column by passing through it, for example, a substance which may be either an aqueous solution of pyrazole or a lower alkanol having at least two carbon atoms. The use of pyrazole for elution results in a ternary mixture or complex of alcohol dehydrogenase, NAD, and pyrazole; and while the alcohol dehydrogenase can readily be separated from NAD by conventional dialysis procedures, separation of the alcohol dehydrogenase from the pyrazole is more difficult and expensive. Consequently, it is preferred, for most purposes, to use a lower alkanol for elution. Methyl alcohol is not satisfactory, but lower alkanols having at least two carbon atoms can be employed such as ethanol, propanol, butanol, pentanol, N-hexanol, 2-ethylhexanol and the like. Although pure alkanols can be used, less expensive mixtures of water with alkanol are preferred, the amount of alkanol being from 0.2 to 0.5 molar. Using these materials, the binary complex of alcohol dehydrogenase and NAD is eluted in high yield and in high concentration. By employing gradient elution using successively higher concentrations of alkanol in separate aqueous phosphate buffer solutions as successive eluants the complex can be fractionated into various isoenzymes or mixtures of isoenzymes as it is eluted.

The pyrazole-insensitive portion of the alcohol dehydrogenase complex, containing the anodic band of alcohol dehydrogenase (II-ADH), passes through the column of affinity resin along with residual foreign proteins. The anodic band can be separated from foreign proteins by salting out, desalting with agarose, then subjecting the salted out portion to affinity chromatography through a column containing agarose-AMP resin to which the anodic band binds and from which it is eluted by an NAD solution gradient.

The following specific examples will illustrate the preparation of the novel affinity resins in which pyrazole is coupled to a support at the 4-position by groups of different lengths, and the use of such resins for purification of alcohol dehydrogenases.

EXAMPLES

In each case, there was used as the insoluble solid support a granular dextran sold under the trade name Sepharose 4B (Pharmacia). A sample of dextran was washed extensively with water, then activated by reacting with an aqueous solution of cyanogen bromide at approximately 20° C., the total volume of the reaction mixture being approximately twice that of the dextran alone and the pH of the mixture being maintained between 10.5 and 11.0 by means of addition of concentrated sodium hydroxide. When the release of protons ceased, the gel was cooled to 4° C. by the addition of ice, transferred to a Buchner funnel and washed with approximately 30 times its volume of 0.1 molar sodium bicarbonate at a temperature of 4° C. The gel after gentle drying by suction was then coupled with the desired pyrazole derivative containing a coupling arm in the 4-position by mixing the gel with an equal volume of aqueous solution containing 0.1 molar sodium bicarbonate at pH 9.5 and the desired pyrazole compound at the desired concentration at 4° C., the mixture being gently stirred by rocking for 48 hours. At the end of this time, the reaction being complete, the gel was washed with aqueous 1 molar sodium chloride solution followed by aqueous 0.05 molar sodium phosphate at pH 7.5. There was added to the finished affinity resin, 0.01% sodium azide as a preservative to prevent microbial growth.

Two series of activated gels were prepared, one using 180 mg. of cyanogen bromide per ml. of dextran, the other employing 300 mg. cyanogen bromide per ml. of dextran. The amount of pyrazole compound reacted with the activated dextran gel support was also varied to provide affinity resins having different binding capacities for the alcohol dehydrogenase.

Pyrazole compounds substituted at the 4-position by difunctional groups of differing chain lengths were prepared as follows, each pyrazole compound having a terminal amino group at the end of the coupling arm for reaction with the activated dextran.

4-(3-aminopropyl)-pyrazole dihydrochloride

Over a 2-hour period, 47 grams of dihydropyrane (0.56 mole) was added dropwise to 240 grams of triethylorthylformate (1.62 moles) and 0.3 ml. of boron trifluoride etherate, the reaction vessel being cooled to maintain the temperature below 40° C. After stirring overnight at 25° C., excess triethylorthylformate was removed by evaporation on a Rotovac and the product was distilled to give 106 grams of clear colorless liquid identified as 2-ethoxy-3-tetrahydropyrane aldehyde diethyl acetal, b.p. 60°-65°/0.2 mm. Hg.

A solution containing 34.5 grams of the acetal (0.158 mole) in 25 ml. ethanol was mixed with a solution containing 19.0 gram of hydrazine dihydrochloride (0.18 mole) in 50 ml. of water. After heating overnight at 40°-50° C., the pH of the homogeneous solution was adjusted to pH 12 by the addition of concentrated sodium hydroxide and volatile material was removed on a Rotovac. The residue was extracted with ethanol to produce, after evaporation of the alcohol, a yellow oil that was distilled (b.p. 141°-143°/0.25 mm. Hg) and identified as 4-(3-hydroxypropyl)-pyrazole; the product was isolated in 70% yield.

The foregoing product, in the amount of 9.0 grams (0.07 mole) was mixed with 35 ml. thionyl chloride, heated at 60° C. for 5 minutes, and then excess thionyl chloride was removed under vacuum at 70° C. to leave a yellow solid which was recrystallized from a mixture of ethanol and ethyl ether to give a white solid identified as 4-(3-chloropropyl)-pyrazole hydrochloride, melting point 113°-114° C. in the amount of 7.7 grams.

This product was converted to 4-(3-phthalimidopropyl)-pyrazole by mixing it with a solution of 17.7 grams of sodium bicarbonate (0.21 mole) and 38.8 grams of potassium phthalimide (0.21 mole) in 200 ml. of dimethylformamide. The mixture was refluxed for 30 minutes, cooled, filtered, then mixed with 500 ml. of water to precipitate a white solid which, after recrystallization from water, was in the form of a white solid melting at 133°-135° C.

This phthalimide intermediate (8.0 1 gram, 0.03 mole) was refluxed in 100 ml. of 6 normal hydrochloric acid overnight. The clear solution was cooled to 4° C., phthalic acid removed by filtration, and the filtrate evaporated to dryness to give a product which, after recrystallization from a mixture of ethanol and ethyl ether, amounted to 4.4 grams of a white solid identified as 4-(3-aminopropyl)-pyrazole dihydrochloride, melting point 189°-190° C. This pyrazole compound could be coupled to the activated dextran by reaction of the terminal amino group, but the resulting affinity resin, in which the coupling arm had a length of only 6 Angstrom units, had poor binding capacity for the binary complex of alcohol dehydrogenase and NAD.

4-[3-(N-6-aminocaproyl)-aminopropyl]-pyrazole

A pyrazole compound for coupling with the activated dextran was prepared from 4-(3-aminopropyl)-pyrazole dihydrochloride by first preparing carbobenzoxy-6-aminocaproic acid by a conventional Schotten-Baumann procedure; 5.1 millimoles of this acid was then reacted with equimolar quantities of N-hydroxysuccinimide and N,N-dicyclohexylcarbodiimide in 100 ml. of a mixture of dry dioxane and dimethoxyethane (10:1) and allowing it to stand overnight at 4° C. The reaction mixture was filtered into 50 ml. of water containing 2.1 grams sodium bicarbonate (20.4 millimoles) and 1.0 gram of 4-(3-aminopropyl)-pyrazole dihydrochloride (5.1 millimoles). After 5 hours, the reaction mixture was acidified with hydrochloric acid, extracted with chloroform, then basified with sodium hydroxide, and extracted with chloroform. These last extracts were combined and dried over magnesium sulfate and the solvent was removed by evaporation on a Rotovac to provide a yield amounting to 80% of the theoretical of a white powder which was recrystallized from a mixture of water and ethanol, melting point 127°-128° C., and determined by elemental analysis, infrared and nuclear magnetic resonance spectra to be 4-[3-(carbobenzoxy-N-6-aminocaproyl)-aminopropyl]-pyrazole. The product was then subjected to catalytic hydrogenation using palladium on charcoal as a catalyst in methanol as solvent. The resulting product was identified as 4-[3-(N-6-aminocaproyl)-aminopropyl]-pyrazole by elemental analysis, infrared and nuclear magnetic resonance spectroscopy. This pyrazole compound possessed a coupling arm having a length of approximately 16 Angstrom units and was reacted with two different samples of activated dextran particles prepared as described above by using 180 mg. and 300 mg. respectively of cyanogen bromide per ml. of dextran particles. There was mixed with the activated dextran an equal volume of aqueous solution containing the pyrazole compound at the desired concentration and the pH of the solution was adjusted to 9.5 with 0.1 molar sodium bicarbonate.

Carbobenzoxy glycine can be substituted for carbobenzoxy-b 6-aminocaproic acid in the foregoing procedure to make 4-[3-(N-2-aminoacetyl)-aminopropyl]-pyrazole having a coupling arm approximately 10 Angstrom units long; an affinity resin made by coupling this pyrazole compound to activated dextran has poor binding capacity for the binary complex. When carbobenzoxy-3-aminopropionic acid is employed, the product, 4-[3-(N-3-aminopropionyl)-aminopropyl]-pyrazole, has a coupling arm 12 Angstrom units long and is effective for the purpose of the present invention when coupled to activated dextran. Other affinity resins can be made by substituting carbobenzoxy-4-aminobutyric acid and carbobenzoxy-5-aminovaleric acid for carbobenzoxy glycine.

4-[3-(6-]p-aminobenzoyl]-N-6-aminocaproyl)-aminopropyl]-pyrazole

There were dissolved in 200 ml. of a mixture of equal volumes of dimethyl formamide and water together with 5 ml. of triethylamine, 52 millimoles each of p-nitrobenzoyl azide and 6-aminocaproic acid at room temperature. After stirring at room temperature for 24 hours, the solution was rendered basic with sodium hydroxide and extracted with chloroform. The solution was then acidified with hydrochloric acid and again extracted with chloroform. The second chloroform extract was dried over sodium sulfate and the solvent was evaporated on a Rotovac to provide in 85% yield a solid melting at 140°–143° C. identified as 6-(p-nitrobenzoyl)-aminocaproic acid. This product was coupled to 4-(3-aminopropyl)-pyrazole by the same procedure described above for coupling carbobenzoxy-6-aminocaproic acid. The product was then subjected to catalytic hydrogenation using palladium on charcoal as catalyst in a solvent consisting of methanol with 1% acetic acid. The product was identified by elemental analysis and infrared spectrum as 4-[3-(6-[p-aminobenzoyl]-N-6-aminocaproyl)-aminopropyl]pyrazole. This pyrazole compound, having a coupling arm approximately 27 Angstrom units in length, was reacted with activated dextran following the same procedure described above.

Binding of the binary complex of alcohol dehydrogenase and NAD, prepared as described above, was carried out by applying the solution to a column containing one of the affinity resins prepared as described above. The column was 0.9 by 20 cm. in dimensions and the solution was applied at a flow rate 1 ml. per minute until no further binding of the alcohol dehydrogenase to the affinity resin occurred. The column was then washed with 20 volumes of an equilibrating buffer solution containing 50 millimoles of phosphate buffer and 0.37 millimoles of NAD per liter of water at pH 7.5.

Elution was carried out using 0.5 molar aqueous ethanol.

In every case, the total alcohol dehydrogenase recovered during the elution step was 90–100% of that bound to the affinity resin, while the overall yield based upon the alcohol dehydrogenase present in the crude extract before treatment with diethylaminoethyl cellulose was from 60 to 90%. The extent of purification is shown by the fact that the specific activity in the eluate was increased by more than 100 fold over the specific activity of the crude extract, and the time required for the purification was markedly less than that required using the procedures of the prior art.

The following table summarizes the results obtained using as the affinity resin dextran (Sepharose 4B) activated with 300 mg. of cyanogen bromide per ml. and reacted with an equal volume of an aqueous solution containing 0.058 molar pyrazole compound at pH 9.5 (0.1 molar bicarbonate). The solution of binary complex contained 0.37 m.molar NAD and 50 m.molar phosphate buffer at pH 7.5. Elution was carried out using 0.5 molar ethanol in water.

| Alcohol Dehydrogenase Source | Specific Activity* U/mg. total protein | | | Yield, Percent |
|---|---|---|---|---|
| | Crude Extract | Solution of Binary Complex | Eluate | |
| Human Liver | 0.021 | 0.210 | 5.7 | 65 |
| Rabbit Liver | 0.012 | 0.024 | 3.6 | 78 |
| Rat Liver | 0.005 | 0.017 | 2.0 | 69 |
| Horse Liver | 0.032 | 0.141 | 14.9 | 88 |

*$\Delta$ 340/min/$A_{280}$

Similar results are obtained using other pyrazole compounds coupled to the dextran such as 4-[3-(6-[p-aminobenzoyl]-N-6-aminocaproyl)-aminopropyl]-pyrazole.

Fractionation of the binary complex bound to the column of affinity resin into three separate fractions each containing a different mixture of isoenzyme complexes with NAD was achieved by washing the column (containing pyrazole-bound complex) with 50 m.molar phosphate buffer, pH 7.5, to remove excess NAD, then eluting with three successive portions of aqueous phosphate buffer, pH 5, containing respectively 10, 50 and 500 m.molar ethanol.

EXAMPLE — Polyacrylamide Support

There was used as the water-insoluble solid support a granular polyacrylamide sold under the trade name Bio-Gel P-100 (Biorad Laboratories). The polyacrylamide particles were first converted to the hydrazide form by conventional methods as described, for example, in Inman and Dintzis, Biochemistry, Vol. 8, pages 4074–4082 (1969). The particulate resin in hydrazide form (10 ml) was washed with 0.3 N hydrochloric acid, then suspended in 18 ml of 0.3 N hydrochloric acid, all at 4° C. To the suspension was added 3 ml. of 1 M sodium nitrite; after 90 seconds there was added 1.5 g of adipate dihydrazide dissolved in 10 ml. of 0.2 M sodium bicarbonate. The pH was adjusted to 9.4 with 4 N sodium hydroxide and the mixture was maintained at 4° C. for three hours; it was then washed with 2 M ammonium chloride and 1 M ammonium hydroxide at pH 9.0 at 4° C. for 10 hours.

The product thus formed was washed with 0.3 M hydrochloric acid and cooled to 4° C. With it was mixed 207 mg of sodium nitrite in 3 ml. of water, and, after 90 seconds, 300 mg of 4-(3-aminopropyl)-pyrazole in 10 ml. of 0.2 M sodium bicarbonate was added, the pH adjusted to 9.4 with 4 M sodium hydroxide, and the mixture stirred for three hours. The product was an affinity resin in which the pyrazole was covalently bonded at the 4-position to the support by a coupling arm or connecting arm or group which was 4-[3-

(adipylhydrazido)-aminopropyl] and which had a length of approximately 16 Angstrom units.

The affinity resin prepared as described above was washed extensively with 0.05 M phosphate at pH 7.5 and then packed into a column 0.9 × 10.5 cm and further equilibrated with a buffer containing 0.2 M sodium chloride, 0.05 M phosphate, 25 mM NAD at pH 7.5. Impure liver alcohol dehydrogenase (specific activity 1.0 unit/$A_{280}$ abs.) was converted into the binary complex in the same buffer used for equilibration as described above, and the solution was applied to the column. After all of the non-adsorbed protein was washed out elution of the binary complex was effected by applying to the column a buffer of the same compositon as used for the equilibration above with the addition of 250 mM ethyl alcohol. The eluted product contained a total of 7 units of activity with a specific activity of 10.5 units/$A_{280}$ abs. Estimated capacity of the column was 200 μg of liver alcohol dehydrogenase per ml. resin.

Similar results can be achieved using other affinity resins in which pyrazole is bonded to other carbohydrate or polyacrylamide water insoluble solid supports through a covalent linkage at the 4-position to a coupling or connecting arm having a length of at least 12 Angstrom units.

The efficiency of a process for purification of an enzyme can be defined as the specific activity of the product multiplied by the yield in percent and divided by the time required for the process in days. In these terms, the efficiency of the prior art processes for concentrating alcohol dehydrogenase from human liver is less than 10, while that of the present invention is of the order of at least 200. In addition, the process of the present invention when used to purify alcohol dehydrogenase from the liver of horses, rats and rabbits provides greatly increased efficiency as compared to processes of the prior art.

The anodic band containing human liver alcohol dehydrogenase which was not bound to the pyrazole affinity resin was prepared as follows.

Starting with 100 g frozen human liver having a specific activity at pH 10 of about 0.05 I.U./mg and low inhibition (~ 75%) by 33 micromolar 4-methylpyrazole at pH 10 as well as high intensity of stain for the anodic band on starch gel electrophoresis, the liver was homogenized in 2.5 volumes water at 4° C., centrifuged for 30 min. at 30,000 rpm in a 30 rotor to provide 240 ml. of clear supernatant assaying at 58 I.U. of pyrazole-insensitive activity with a specific activity of 0.002 I.U./mg.

The crude supernatant was aspirated through a bed containing 2.5 ml. diethylaminoethyl cellulose (Whatman DE-52) per g liver in a 4.5 × 10 cm column equilibrated with 10 millimolar Tris-Cl, pH 7.9 and 0.4 mMHO at 25° C. The resin bed was washed with one volume of buffer, and after discarding the void volume (about 100 ml.), the effluent containing the alcohol dehydrogenase was collected, recovery being 100% with a 17.5-fold purification. The starch gel pattern of the product, as developed by the activity stain Nitroblue Tetrazolium, was identical to that of the crude extract.

The effluent was equilibrated with 50 millimolar sodium phosphate and 1.2 millimolar $NAD^+$, pH 7.5 at 25° C. to form the binary complex of alcohol dehydrogenase and NAD. The binary complex was then applied to the 4-[3-(N-6-aminocaproyl)aminopropyl]pyrazole dextran resin prepared as described above using 2 ml. resin per g liver and applying the solution at the rate of 10 ml./min. The affinity resin was then washed with the same buffer, 50 millimolar phosphate and 1.2 millimolar NAD pH 7.5.

The eluant buffer solution contained, in 330 ml. (fractions 11 to 32), the anodic band of the alcohol dehydrogenase. About 52% of the activity was recovered in the eluant, having a specific activity of 0.033 I.U./mg. This material was not inhibited by 4-methyl-pyrazole (95–100% Vi/Vc).

The eluant solution was concentrated to 40 ml. at 4° C. by ultrafiltration to remove the aqueous medium through a permeable membrane (Amicon PM-10) to an absorbance ratio 280/260 of 0.8, indicating the presence of $NAD^+$.

The concentrate was adjusted to 0.1 molar in Tris-Cl buffer, pH 8.6 at 4° C., solid ammonium sulfate (0.5 g/ml. 70% saturation) was added, and the solution stirred for 45 min. at 4° C. to form a precipitate by salting out effect. After centrifugation for 30 min. at 30,000 rpm in a 30 rotor, the resulting pellet was dissolved in 40 ml. of 5 millimolar Tris-Cl, pH 7.2 at 25° C., then desalted over an agarose (Sephadex G-25) column 5 × 50 Cm equilibrated with 0.1 molar Tris-Cl, pH 8.6 at 4° C. The absorbance ratio 280/260 of the resulting material was 1.6 to 1.7, indicating absence of coenzyme. Moreover, 80% of the activity was recovered with a two-fold purification.

The solution thus prepared was applied to a 2.5 cm column packed with 1 to 2 ml. per I.U. of activity (approximately 40 ml.) of agarose-adenosine monophosphate resin (P-L Biochemicals AMP type 2) equilibrated with 0.2 molar Tris-Cl, pH 8.6 at 4° C. All of the alcohol dehydrogenase (anodic band) bound to the resin while a large amount of extraneous protein passed through with the effluent. The column was washed with buffer at 1 ml./min until the absorbance at 280 nm approached zero.

The pyrazole-insensitive fraction of the alcohol dehydrogenase (anodic band) was then eluted from the column with a 0 to 7 × $10^{-5}$ molar gradient NAD solution.

The procedure is summarized in Table 1 below:

Table 1

Purification of Pyrazole Insensitive Human LADH Isozyme

| Step | Volume (ml) | Protein[a] (mg) | Pyrazole-Insensitive Activity (IU) | Specific Activity (IU/mg) | Yield (%) | Purification (fold) |
|---|---|---|---|---|---|---|
| Crude Extract | 230 | 25,300 | 58[b] | 0.002 | 100 | 1 |
| DEAE Effluent | 380 | 1,780 | 59 | 0.035 | 100 | 17.5 |
| CapGapp Effluent | 330 | 630 | 30[c] | 0.033 | 52 | 16.5 |
| Ammonium Sulfate Precipitate | 40 | 330 | 24 | 0.072 | 41 | 36 |
| Agarose-AMP | 25 | 18 | 20 | 1.1 | 34 | 550 |

[a]$E_{280nm}^{0.1\%} = 0.58$
[b]257 I.U. of Pyrazole-sensitive activity also present
[c]No pyrazole-sensitive activity present The product was virtually uninhibited by 33 micromolar 4-methyl-pyrazole and exhibited no lactate dehydrogenase activity. When subjected to sodium dodecyl sulfate disc gel electrophoresis a single species was found, demonstrating molecular weight homogeneity of the product. Its mobility was indistinguishable from that of commercially available horse liver alcohol dehydrogenase. The isozyme product under dissociative conditions, i.e., sodium dodecyl sulfate and beta-mercaptoethanol, displayed a molecular weight of 42,000; under non-dissociative conditions, i.e., 0.01 molar Tris-Cl and 0.1 molar KCl, pH 7.5 sedimentation equilibrium by the Yphantis method gave a linear plot of log $[Y(r)-Y_o]$ versus $r^2$, the plot having a slope of 1.184 corresponding to a molecular weight of 78,000.

From 100 g of liver there was obtained by the foregoing procedure 18 mg of pyrazole insensitive alcohol dehydrogenase having a specific activity of 1.1 I.U./mg with an overall yield of 34% and 550-fold purification.

Sodium dodecyl sulfate starch disc gel electrophoresis of the product at pH 7.7 showed a single species staining for alcohol dehydrogenase activity which migrated toward the cathode, was more anodic than the pyrazole-bound isozymes described below, and corresponded to the anodic band of Li et al. It exhibited no alcohol dehydrogenase activity, and when subjected to isoelectric focusing in polyacrylamide gel, stained for protein in the pH range 3 to 10, appeared at about pH 9 in the gradient, with no species having an isoelectric point less than about 8.5.

The zinc content of the product was measured by atomic absorption spectrometry and found to be 3620 micrograms per gram of protein, corresponding to 4.5 g-atom of zinc per mole of enzyme molecular weight 84,000.

Amino acid composition determined after 24, 48 and 72 hours hydrolysis based upon an assumed molecular weight of 84,000 is shown in Table 2 below.

Table 2

| Amino Acid Composition: Human LADH | | |
|---|---|---|
| Residue | Pyrazole Insensitive | Pyrazole Binding |
| Asp | 33 | 31 |
| Thr | 23 | 23 |
| Ser | 24 | 24 |
| Glu | 29 | 29 |
| Pro | 20 | 21 |
| Gly | 40 | 40 |
| Ala | 36 | 33 |
| Val | 29 | 40 |
| Met | 4 | 7 |
| Ile | 27 | 23 |
| Leu | 30 | 29 |
| Tyr | 5 | 6 |
| Phe | 17 | 17 |
| His | 7 | 6 |
| Lys | 32 | 33 |
| Arg | 8 | 11 |

What is claimed is:

1. The process of purifying and fractionating crude alcohol dehydrogenase extract which comprises mixing said dehydrogenase extract with an aqueous solution containing NAD at a concentration of at least $10^{-4.5}$ molar and at a pH up to 8.0, to form a binary complex of said dehydrogenase with said NAD, bringing said mixture into contact with an affinity resin comprising pyrazole immobilized on an insoluble solid support, said pyrazole being covalently bonded at the 4-position to said support by a connecting arm having a length of at least 12 Angstrom units, to bind a pyrazole-binding fraction of said dehydrogenase and said NAD to said support, and separating said mixture containing the remaining pyrazole-insensitive fraction of said dehydrogenase from said resin.

2. The process as claimed in claim 1 including the additional step of eluting said pyrazole-binding dehydrogenase fraction and said NAD from said resin.

3. The process as claimed in claim 2 in which said elution is carried out with a member of the group consisting of pyrazole and a lower alkanol having at least two carbon atoms.

4. The process as claimed in claim 2 in which said elution is carried out with a lower alkanol having from two to five carbon atoms.

5. The process as claimed in claim 1 in which said connecting arm is 4-[3-(N-6-aminocaproyl)-amino-propyl].

6. The process as claimed in claim 1 in which said connecting arm is 4-[3-(6-[p-aminobenzoyl]-N-6-aminocapropyl)-aminopropyl].

7. The process as claimed in claim 1 in which said crude alcohol dehydrogenase is extracted from liver.

8. The process as claimed in claim 4 in which said crude alcohol dehydrogenase is extracted from liver.

9. The process as claimed in claim 8 in which said connecting arm is 4-[3-(N-6-aminocaproyl)-amino-propyl].

10. The process as claimed in claim 8 in which said connecting arm is 4-[3-(6-[p-aminobenzoyl]-N-6-aminocaproyl)-amino-propyl].

11. The process as claimed in claim 1 in which said crude alcohol dehydrogenase is extracted from human liver and in which said mixture containing pyrazole-insensitive fraction is subjected, after separation from said resin, to salting out to form a precipitate and the precipitate is chromatographed to separate the anodic band of liver alcohol dehydrogenase.

* * * * *

UNITED STATES PATENT AND TRADEMARK OFFICE
CERTIFICATE OF CORRECTION

PATENT NO. : 4,111,751
DATED : September 5, 1978
INVENTOR(S) : Louis G. Lange, III et al.

It is certified that error appears in the above-identified patent and that said Letters Patent are hereby corrected as shown below:

Column 2, line 68, "10-6)" should be "$10^{-6}$)";

Column 6, line 22, "(8.0 1 gram," should be "(8.0 gram,";

Column 7, line 10, delete "b" after "bobenzoxy-";

Column 7, line 25, "4-[3-(6-]p-" should be "4-[3-(6-[p-".

*Signed and Sealed this*

*Sixth* Day of *March 1979*

[SEAL]

Attest:

RUTH C. MASON
*Attesting Officer*

DONALD W. BANNER
*Commissioner of Patents and Trademarks*